(12) United States Patent
Dant

(10) Patent No.: US 7,637,918 B2
(45) Date of Patent: Dec. 29, 2009

(54) HELICAL SUTURING DEVICE

(75) Inventor: Jack A. Dant, St. Paul, MN (US)

(73) Assignee: Zimmer Spine, Inc., Minneapolis, MN (US)

( * ) Notice: Subject to any disclaimer, the term of this patent is extended or adjusted under 35 U.S.C. 154(b) by 508 days.

(21) Appl. No.: 11/201,568

(22) Filed: Aug. 11, 2005

(65) Prior Publication Data

US 2006/0036265 A1  Feb. 16, 2006

Related U.S. Application Data

(60) Provisional application No. 60/601,800, filed on Aug. 16, 2004.

(51) Int. Cl.
*A61B 17/04* (2006.01)
*A61B 17/12* (2006.01)

(52) U.S. Cl. ....................... 606/144; 606/223

(58) Field of Classification Search .......... 606/148, 606/138, 144, 222, 224, 232, 223, 225, 227; 604/264; 112/169, 171, 222, 224; 223/99
See application file for complete search history.

(56) References Cited

U.S. PATENT DOCUMENTS

| | | | |
|---|---|---|---|
| 67,545 A | 8/1867 | Hodgins | |
| 919,138 A | 5/1909 | Drake et al. | |
| 1,583,271 A | 5/1926 | Biro | |
| 2,327,353 A | 8/1943 | Karle | |
| 2,959,172 A | 11/1960 | Held | |
| 4,440,171 A | 4/1984 | Nomoto et al. | |
| 4,465,070 A | 8/1984 | Eguchi | |
| 4,596,249 A | 6/1986 | Freda et al. | |
| 4,641,652 A | 2/1987 | Hutterer et al. | |
| 4,770,652 A | 9/1988 | Mahurkar | |
| 5,018,530 A | 5/1991 | Rank et al. | |
| 5,100,418 A | 3/1992 | Yoon et al. | |
| 5,129,912 A | 7/1992 | Noda et al. | |
| 5,152,769 A | 10/1992 | Baber | |
| 5,176,691 A | 1/1993 | Pierce | |
| 5,269,791 A | 12/1993 | Mayzels et al. | |
| 5,281,237 A | 1/1994 | Gimpelson | |
| 5,330,503 A | 7/1994 | Yoon | |
| 5,336,231 A | 8/1994 | Adair | |
| 5,356,424 A * | 10/1994 | Buzerak et al. | ............. 606/223 |
| 5,368,595 A | 11/1994 | Lewis | |

(Continued)

FOREIGN PATENT DOCUMENTS

EP    0 557 894 A1    2/1993

(Continued)

*Primary Examiner*—Todd E Manahan
*Assistant Examiner*—Erin Colello
(74) *Attorney, Agent, or Firm*—Crompton, Seager & Tufte, LLC.

(57) ABSTRACT

An apparatus for repairing a tear in an annulus fibrosus of a spinal disc includes a hollow, helically-shaped suturing needle and a retriever. The needle is used to insert a suture along a helical pathway bridging the tear. The retriever is used to retrieve one end of the suture from the inside of the annulus and bring it close the other end of the suture outside the annulus, where the suture can be tensioned and tied to fixate the tear. In other embodiments, multiple sutures are placed with helically-shaped needles of differing dimensions.

2 Claims, 7 Drawing Sheets

U.S. PATENT DOCUMENTS

| | | |
|---|---|---|
| 5,387,221 A | 2/1995 | Bisgaard |
| 5,397,326 A | 3/1995 | Mangum |
| 5,405,376 A * | 4/1995 | Mulier et al. ............... 607/127 |
| 5,423,836 A | 6/1995 | Brown |
| 5,433,728 A | 7/1995 | Kim |
| 5,499,991 A * | 3/1996 | Garman et al. ............. 606/148 |
| 5,507,743 A * | 4/1996 | Edwards et al. .............. 606/41 |
| 5,520,703 A | 5/1996 | Essig et al. |
| 5,527,322 A | 6/1996 | Klein et al. |
| 5,545,148 A | 8/1996 | Wurster |
| 5,562,685 A | 10/1996 | Mollenauer et al. |
| 5,575,800 A | 11/1996 | Gordon |
| 5,582,616 A | 12/1996 | Bolduc et al. |
| 5,649,939 A * | 7/1997 | Reddick .................... 606/148 |
| 5,653,716 A * | 8/1997 | Malo et al. ................. 606/139 |
| 5,662,683 A * | 9/1997 | Kay ........................... 606/232 |
| 5,695,462 A | 12/1997 | Sutcu et al. |
| 5,709,692 A * | 1/1998 | Mollenauer et al. ......... 606/141 |
| 5,797,928 A | 8/1998 | Kogasaka |
| 5,810,851 A * | 9/1998 | Yoon .......................... 606/148 |
| 5,814,065 A | 9/1998 | Diaz |
| 5,820,631 A | 10/1998 | Nobles |
| RE36,020 E | 12/1998 | Moore et al. |
| 5,860,992 A | 1/1999 | Daniel et al. |
| 5,899,911 A | 5/1999 | Carter |
| 5,935,138 A | 8/1999 | McJames, II et al. |
| 5,947,983 A | 9/1999 | Solar et al. |
| 6,117,145 A * | 9/2000 | Wood et al. ................. 606/148 |
| 6,280,441 B1 * | 8/2001 | Ryan .......................... 606/45 |
| 6,315,784 B1 | 11/2001 | Djurovic |
| 6,398,796 B2 | 6/2002 | Levinson |
| 6,514,263 B1 | 2/2003 | Stefanchik et al. |
| 6,520,973 B1 | 2/2003 | McGarry |
| 6,530,933 B1 | 3/2003 | Yeung et al. |
| 6,537,248 B2 | 3/2003 | Mulier et al. |
| 6,547,810 B1 | 4/2003 | Sharkey et al. |
| 6,613,058 B1 | 9/2003 | Goldin |
| 6,626,917 B1 * | 9/2003 | Craig ......................... 606/144 |
| 6,663,633 B1 * | 12/2003 | Pierson, III ................. 606/148 |
| 6,689,168 B2 | 2/2004 | Lieberman |
| 6,723,107 B1 | 4/2004 | Skiba et al. |
| 2002/0007218 A1 | 1/2002 | Cauthen |
| 2002/0049439 A1 | 4/2002 | Mulier et al. |
| 2002/0055759 A1 * | 5/2002 | Shibuya ..................... 606/231 |
| 2002/0058967 A1 | 5/2002 | Jervis |
| 2002/0147461 A1 | 10/2002 | Aldrich et al. |
| 2002/0183733 A1 | 12/2002 | Mulier et al. |
| 2002/0198542 A1 * | 12/2002 | Yamamoto et al. .......... 606/144 |
| 2003/0009179 A1 | 1/2003 | Craig |
| 2003/0009227 A1 | 1/2003 | Lambrecht et al. |
| 2003/0153931 A1 | 8/2003 | Schraft et al. |
| 2003/0153976 A1 | 8/2003 | Cauthen, III et al. |
| 2003/0181913 A1 | 9/2003 | Lieberman |
| 2004/0002699 A1 * | 1/2004 | Ryan et al. ................... 606/27 |
| 2004/0034370 A1 | 2/2004 | Rehil |
| 2004/0138693 A1 * | 7/2004 | Eskuri et al. ................ 606/200 |
| 2004/0147957 A1 * | 7/2004 | Pierson, III ................. 606/228 |
| 2005/0228406 A1 * | 10/2005 | Bose .......................... 606/144 |
| 2005/0283193 A1 * | 12/2005 | Tullberg et al. ............. 606/232 |

FOREIGN PATENT DOCUMENTS

| | | |
|---|---|---|
| JP | 2001-198132 | 7/2001 |
| WO | WO 01/30245 A1 * | 5/2001 |
| WO | WO 03/099137 A2 | 12/2003 |
| WO | WO 2004/002550 A2 | 1/2004 |
| WO | WO 2004004577 A2 * | 1/2004 |

* cited by examiner

HELICAL SUTURING DEVICE

CROSS-REFERENCE TO RELATED APPLICATIONS

This application claims priority from U.S. Provisional Patent Application No. 60/601,800, filed on Aug. 16, 2004, entitled "Helical Suturing Device", which is incorporated herein by reference in its entirety.

TECHNICAL FIELD

The present invention is related to medical devices for suturing. More particularly, it relates to devices for repairing a tear in the annulus fibrosus of a spinal disc.

BACKGROUND

The intervertebral discs are ligaments that connect the vertebrae of the spine together. They provide structural support for the spine and distribute forces exerted on the spinal column. An intervertebral disc consists of three major components: cartilage endplates, nucleus pulposus, and annulus fibrosus. The central portion, nucleus pulposus, is relatively soft and gelatinous, having a consistency similar to that of crabmeat. Surrounding the nucleus is the annulus fibrosus, which has a more rigid consistency and is largely comprised of concentric layers of fibrous tissue. The annular portion serves to provide peripheral mechanical support to the disc, afford torsional resistance, and contain the softer nuclear portion and resist its hydrostatic pressure.

Unfortunately, intervertebral discs are susceptible to injury. Disc herniation occurs when the nucleus begins to extrude through an opening in the annulus, often to the extent that the herniated material impinges on nerve roots in the spine, resulting in pain. One way to address such pain is remove the bulging disk material surgically through a nucleotomy and/or anulotomy, thus relieving pressure on the nerve roots. Further treatment might include the use of intervertebral spacers to reduce the pressure exerted on the disc by the spine. However, very few products are currently available that address the repair of the annulus fibrosus per se. This is true whether the annular tissue has been damaged by herniation, or by the creation of surgical access ports in the course of disc repair.

There exists a need for methods and instruments for repair of the annulus fibrosus. Any such methods that are simple and compatible with minimally-invasive surgical techniques would be particularly desirable.

SUMMARY

The present invention, according to one embodiment, is a system for repairing a tear in an annulus fibrosus of a spine. The system includes a substantially helically-shaped suturing needle, a length of suture, and a retriever. The suturing needle is configured to deliver the suture in a helically-shaped path bridging the tear. The retriever is configured to retrieve one end of the suture from the inside of the annulus to the outside, where the two ends of the suture can be tensioned and tied. In other embodiments, multiple systems are used to place multiple sutures.

This summary is not intended to describe each embodiment or every implementation of the present invention. A more complete understanding of the invention will become apparent upon review of the detailed description and listing of embodiments in conjunction with the accompanying drawings. As will be realized, the invention is capable of modifications in various obvious aspects, all without departing from the spirit and scope of the present invention. Accordingly, the drawings and detailed description are to be regarded as illustrative in nature and not restrictive.

DETAILED DESCRIPTION

Figure 1:
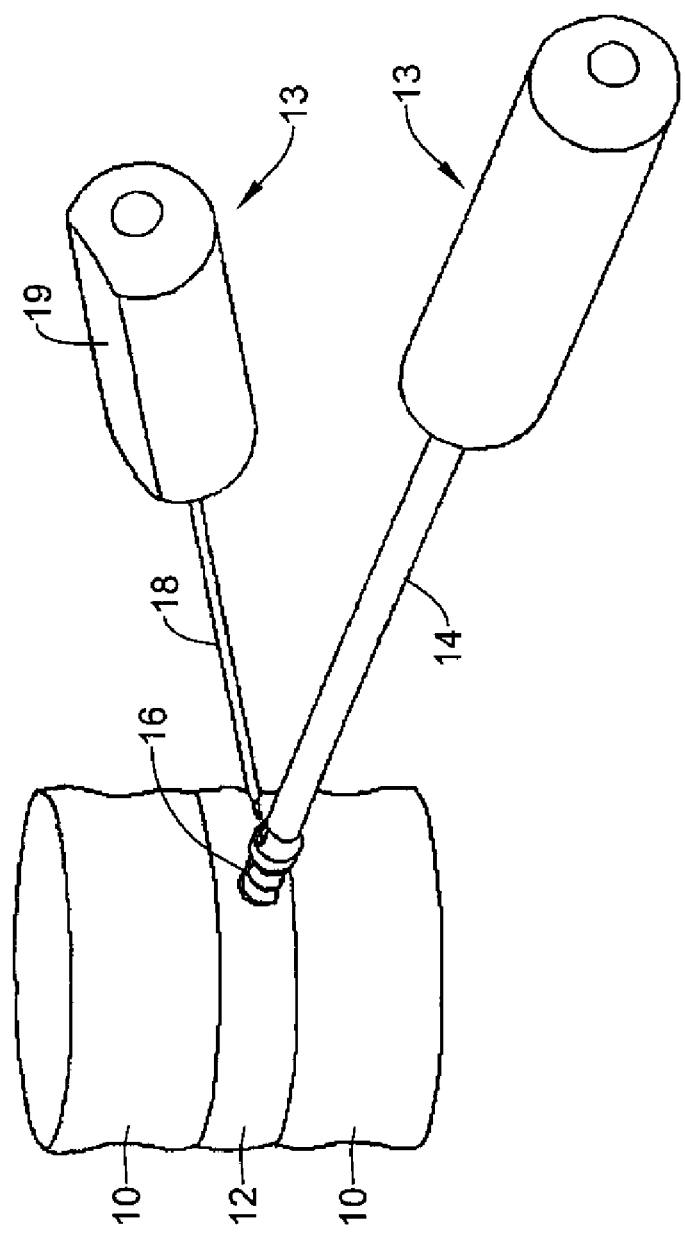
FIG. 1 is an illustration of a representative section of human spine having two vertebrae and a disc with a set of tools for suturing the disc according to one embodiment of the present invention.

The present invention, in one embodiment, is directed to the repair of tears, cuts, voids, or like tissue damage in discs of the spine. FIG. 1 illustrates a simplified representation of a section of spine including two vertebrae 10 between which is seen an annulus fibrosus 12 of a spinal disc. Major components of an apparatus 13 for repairing an annulus 12 are also shown. A needle handle 14 manipulates a helical suturing needle 16 engaged with the annulus 12. A suture retriever 18 is shown above the needle handle 14. The suture retriever 18 has a flat 19 to indicate its rotational orientation.

Figure 2:
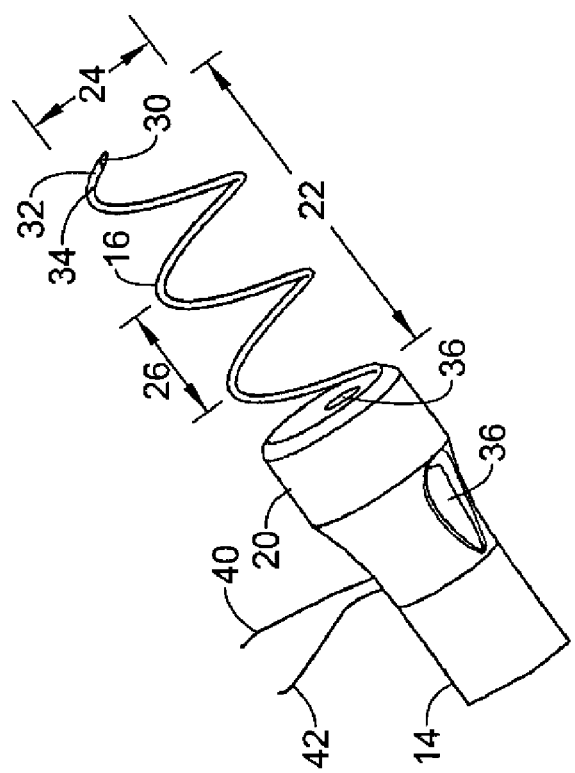
FIG. 2 is a perspective detail view of the helically-shaped suturing needle and needle handle shown in FIG. 1.

FIG. 2 is a perspective view of a distal end 20 of the needle handle 14 attached to a helical suturing needle 16. The helical needle 16 can be characterized by a longitudinal depth 22, a diameter 24, and a pitch 26. In one embodiment, the needle 14 is hollow, having a central lumen that communicates with three bores in the needle, a first bore (not shown) at a proximal end (not shown; located in the needle handle 14) of the needle, a second bore 30 at a distal end 32, and a third bore 34 near the distal end. (See FIG. 3 for an enlarged view of the bores 30, 34.) The needle handle 14 also features a retriever guide 36 that facilitates use of the suture retriever 18.

The chosen values of the depth 22, diameter 24, and pitch 26 of a helical suturing needle 16 will vary with the particular injury to be repaired, the location of the disc along the spine, and the particularities of the individual patient. According to one embodiment, the depth 22 of the needle 16 will have a value ranging from about 3 mm to about 25 mm, the diameter 24 will have a value ranging from about 2 mm to about 13 mm, or, alternatively, from about 2 mm to about 19 mm, and the pitch 26 will have a value ranging from about 2 mm per turn to about 7 mm per turn. According to another embodiment, the needle 16 has a depth 22 of about 11 mm and a diameter 24 of about 7 mm. According to still another embodiment, the needle 16 has a depth 22 of about 5 mm and a diameter 24 of about 3 mm.

Figure 3:
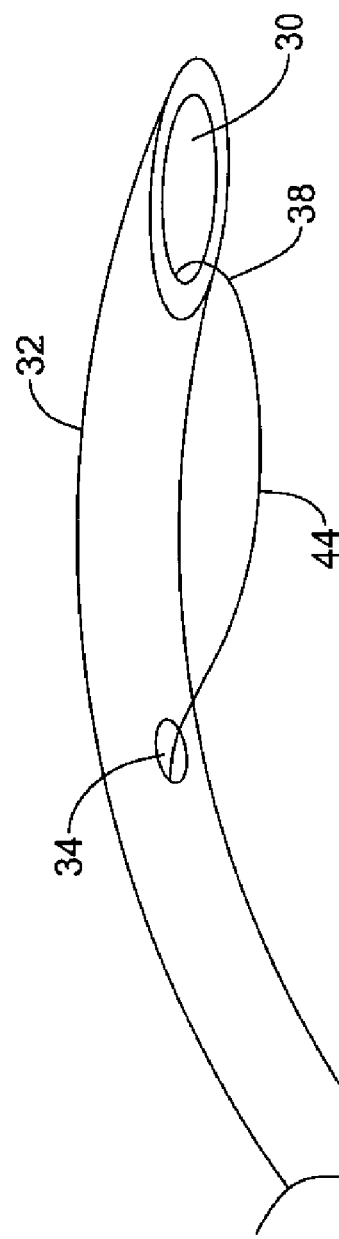
FIG. 3 is a detailed view of the distal end of the helically-shaped suturing needle shown in FIGS. 1 and 2.

FIG. 3 is an enlarged perspective view of the distal end 32 of the helical needle 16. Prior to use, a length of suture 38 is loaded in the helical needle 16 such that it runs from the first bore (not shown) up the needle to the second bore 30, exits the needle there and reenters the needle at the third bore 34, whereupon it runs down the needle back to the first bore. The suture 38 may be loaded during the manufacturing of the helical needle 16 or may be inserted by the surgeon using a push rod (now shown) or some other method of passing the suture 38 through the helical needle 16. In this configuration, both a first end 40 and a second end 42 of the suture 38 extend out of the first bore of the helical needle near the distal end 20 of the needle handle 14, where they can be manipulated by a surgeon (see FIG. 2). The second 30 and third 34 bores of the helical needle hold the suture 38 such that a capturable segment 44 of the suture is formed.

Figure 4:
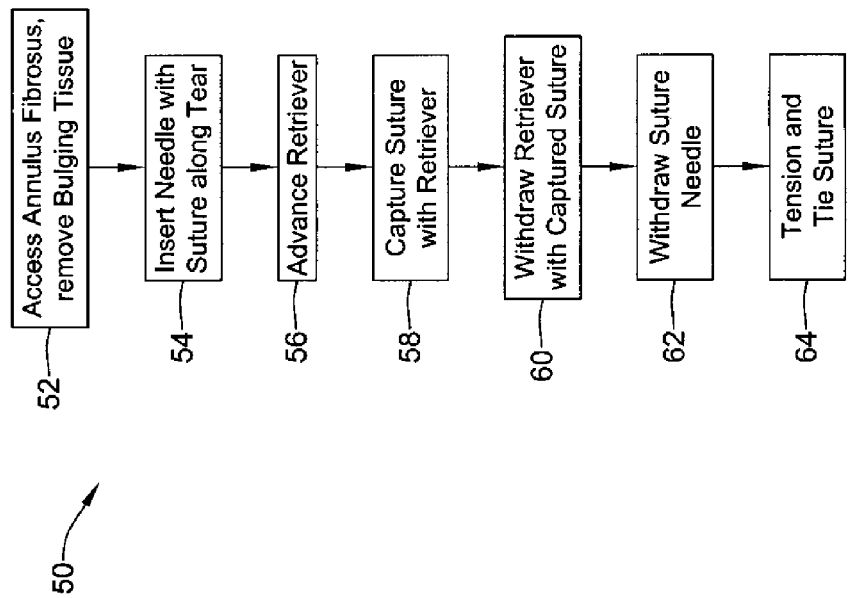
FIG. 4 is a flowchart describing a method of repairing an annulus fibrosus according to one embodiment of the present invention.
Figure 5:
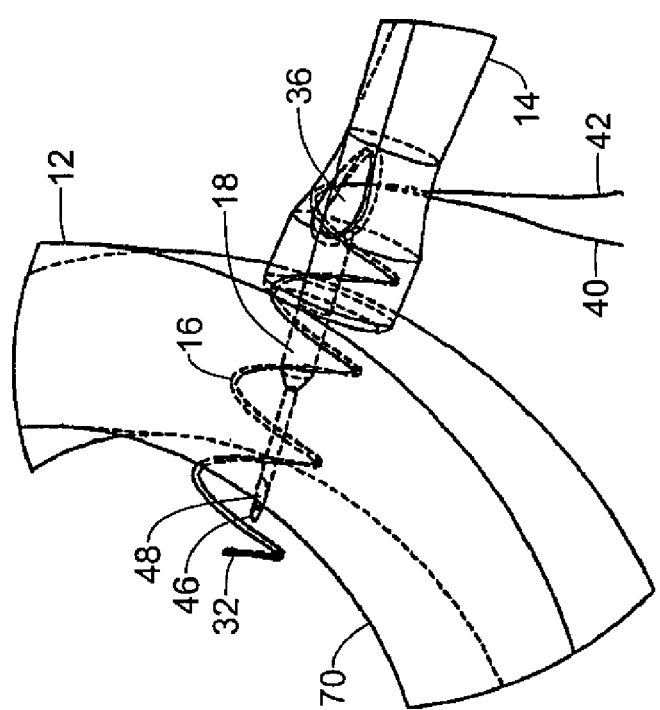
FIG. 5 illustrates a helically-shaped needle, needle handle, and retriever in relation to each other and a representative disc undergoing repair.
Figure 6:
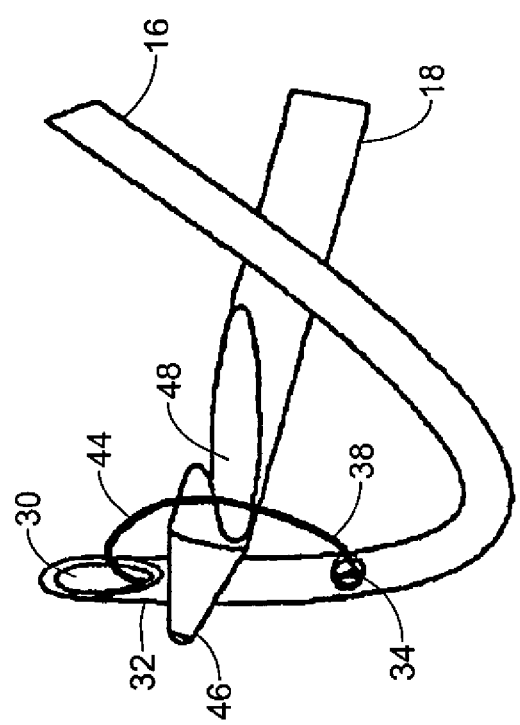
FIG. 6 is a detailed view of the distal ends of the helically-shaped needle and retriever illustrated in FIGS. 1-4.

A method 50 for using the present invention according to one embodiment to repair an annulus fibrosus 12 is summarized in the flowchart of FIG. 4. The method may be better understood by referring also to FIG. 5, which illustrates the situation mid-way through the procedure at block 56, and FIG. 6, an enlarged view of the distal ends (32, 46) of the helical needle 16 and suture retriever 18, along with this description.

Standard surgical techniques are used to gain access to the annulus fibrosus 12, and if necessary, a nucleotomy and/or an anulotomy are performed to remove bulging disc tissue (block 52). Any appropriate conventional or otherwise known techniques can be used for these purposes. A surgeon inserts a helical suturing needle 16, preloaded with suture 38, along a tear (not shown for clarity) in the manner of a corkscrew by rotating the needle handle 14 such that the helix is centered on the tear and the needle penetrates tissue along opposing sides of the tear (block 54). The insertion is continued until the distal end 32 of the needle 16 reaches an interior region 70 of the annulus fibrosus 12.

After the insertion of the needle 16, the suture retriever 18 is advanced into the annulus 12 (block 56), guided by the retriever guide 36 of the needle handle 14. During this step, the surgeon holds the first 40 and second 42 ends of the suture 38 taut to maintain the capturable segment 44 in a well-defined position relative to the needle 16 and handle 14. The retriever 18 and guide 36 are tightly toleranced such that the distal end 46 of the suture retriever 18 is reliably brought to the capturable segment 44. A hook 48 at the distal end 46 of the retriever 18 captures the capturable segment 44 (block 58).

To aid in this capture process, in some embodiments, the retriever 18 and guide 36 include corresponding structures to stop the motion of the retriever in the distal direction once the distal end 46 of the retriever reaches the capturable segment 44. Also in some embodiments, the retriever 18 and guide 36 include corresponding structures to restrict the rotational orientation of the retriever relative to the needle handle 14 and helical suturing needle 16.

Figure 7:
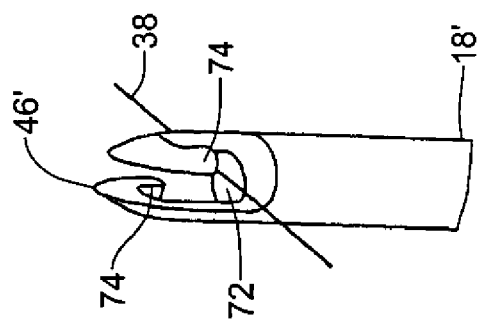
FIG. 7 is a set of detailed views of an alternate distal end for the retriever.
Figure 7:
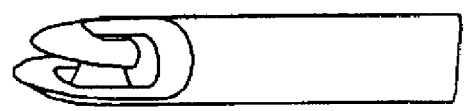
Figure 7:

In another embodiment of the present invention, illustrated in FIG. 7, a suture retriever 18' has double opposing hooks 74 for capturing the suture at its distal end 46'. In this version, the retriever 18' is advanced so that the suture 38 fully enters the slot 72. The surgeon then rotates the retriever 18' about 90 degrees and withdraws it. The hooks 74 ensure that the suture 38 remains captured during the withdrawal.

Following capture of the suture 38, the surgeon releases the first end 40 of the suture while maintaining a grip on the second end 42. Then he or she withdraws the retriever 18, which pulls the first end 40 of the suture 38 out of the annulus fibrosus 12 along the interior of the helical pathway defined by the suturing needle 16 (block 60). The surgeon then grips the first end 40, releases the second end 42, and retracts the helical suturing needle 16 in a reverse screwing motion, leaving suture 38 along its path (block 62).

With the helical needle 16 completely removed from the annulus fibrosus 12, the suture 38 remaining in the needle is freed by further withdrawal of the needle, or alternately the suture is simply cut between the needle and the annulus. The surgeon starts tying the suture 38 with an overhand knot, carefully applies tension to draw the tear of the annulus 12 together, completes the knot as per standard surgical technique, and cuts off the excess suture (block 64).

While the preceding method describes repair of a tear in an annulus fibrosus oriented in a predominantly radial direction, the present invention may also be used to repair tears with other orientations, such as parallel to the outer surface of an annulus. Furthermore, the present invention may be usefully employed in other anatomies as well.

The present invention leaves only suture as the final implanted material. Suture is equally distributed over the entire depth of the tear, and acts to close the tear from all directions. The present invention offers improved resistance to recurrence of herniation over prior suturing methods.

In other embodiments of the present invention, the above described procedure is performed more than once on the same tissue, with different helical suture needles 16, and hence, different paths for the sutures 38, potentially resulting in more secure fixation. For example, two sutures 38 may be concentrically placed with two diameters 24 of needles 16. Alternately, two sutures 38 may be placed with two needles 16 of identical dimensions 22, 24, 26 but having differing right- and left-handed helical shapes. In these embodiments, associated sets of sutures 38 and tools 14, 18 may be given corresponding visual appearances (e.g., colors) to assist surgeons with identification.

In yet other embodiments of the present invention, the suture material includes a bioactive material. The bioactive material may be used to deliver a drug therapy. It may include antibiotic and/or antiviral medications. It may include drugs that promote regenerative growth of the tissues of the annulus fibrosus or other tissues. It may include cultured cells to enhance the healing process.

Various modifications and additions can be made to the exemplary embodiments discussed without departing from the scope of the present invention. Accordingly, the scope of the present invention is intended to embrace all such alternatives, modifications, and variations as fall within the scope of the disclosure, together with all equivalents thereof.

The invention claimed is:

1. An apparatus for fixation of a soft tissue tear comprising:
    a substantially helically-shaped suturing needle including:
    a plurality of helical loops between a distal end and a proximal end, the loops defining an interior region and an exterior region, dimensioned such that when the needle is inserted in the manner of a corkscrew along the tissue tear, at least some of the loops will bridge the tear and the majority of the tear will reside in the interior region of the helical loops;
    a lumen extending substantially from the distal end to the proximal end; and
    three bores communicating with the lumen, a first bore at or near the proximal end, a second bore at or near the distal end, and a third bore between the first and second bores and essentially adjacent to the second bore;
    a length of suture material having a first end and a second end, the suture material positioned so that it enters the lumen of the needle at the first bore, extends within the lumen from the first bore to the second bore, exits the needle at the second bore, reenters the lumen at the third bore, further extends within the lumen to the first bore, and exits the needle at the first bore, arranged so that both the first and the second ends of the suture material protrude from the first bore at or near the proximal end of the needle, and when the first and second ends of the suture material are held taut, the second and third bores of the needle support a capturable segment of the suture material;

a retriever comprising an elongated rod including a distal end and a proximal end, the distal end having a hook capable of capturing the capturable segment of the suture material; and a needle handle fitted to the proximal end of the needle, the needle handle having a retriever guide, the retriever guide slidably connectable to the retriever and formed to constrain the motion of the distal end of the elongated rod of the retriever along a path within the interior region of the helical loops of the needle up to a point at or near the distal end of the needle, where the hook of the rod of the retriever may capture the capturable segment of the suture material.

2. A method of repairing a soft tissue tear comprising:

inserting a helically-shaped needle containing a suture along the soft tissue tear, the needle including a plurality of helical loops defining an interior region, a lumen extending substantially from a distal end to a proximal end, and three bores communicating with the lumen, wherein a first bore is at or near the proximal end, a second bore is at or near the distal end, and a third bore is between the first and second bores and essentially adjacent to the second bore, wherein the suture is positioned so that it enters the lumen of the needle at the first bore, extends within the lumen from the first bore to the second bore, exits the needle at the second bore, reenters the lumen at the third bore, further extends within the lumen to the first bore, and exits the needle at the first bore, arranged so that both the first and the second ends of the suture protrude from the first bore at or near the proximal end of the needle, wherein the first and second ends of the suture material are held taut such that the second and third bores of the needle create a protruding portion of the suture material near the distal end of the needle;

advancing a retriever into the soft tissue tear and through the helical loops of the helically-shaped needle;

capturing the protruding portion of the suture with the retriever;

withdrawing the retriever with the protruding portion of the suture;

withdrawing the helically-shaped needle;

exerting a desired tension on the suture; and tying the suture.

* * * * *

UNITED STATES PATENT AND TRADEMARK OFFICE
CERTIFICATE OF CORRECTION

PATENT NO.      : 7,637,918 B2                                        Page 1 of 1
APPLICATION NO. : 11/201568
DATED           : December 29, 2009
INVENTOR(S)     : Jack A. Dant It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1004 days.

Signed and Sealed this

Ninth Day of November, 2010

David J. Kappos
*Director of the United States Patent and Trademark Office*